US 9,572,419 B2
(12) United States Patent
Bloch et al.

(10) Patent No.: US 9,572,419 B2
(45) Date of Patent: Feb. 21, 2017

(54) ORAL CARE IMPLEMENT HAVING PRESSURE SENSOR AND METHOD OF FORMING THE SAME

(71) Applicant: COLGATE-PALMOLIVE COMPANY, New York, NY (US)

(72) Inventors: Brian Bloch, Hillsborough, NJ (US); Lars Ralf Rainer Lieberwirth, Glashuetten (DE)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/653,884

(22) PCT Filed: Mar. 18, 2013

(86) PCT No.: PCT/US2013/032762
§ 371 (c)(1),
(2) Date: Jun. 19, 2015

(87) PCT Pub. No.: WO2014/098948
PCT Pub. Date: Jun. 26, 2014

(65) Prior Publication Data
US 2015/0327668 A1 Nov. 19, 2015

(30) Foreign Application Priority Data
Dec. 21, 2012 (CN) .......................... 2012 1 0596540

(51) Int. Cl.
*A46B 15/00* (2006.01)
*A61C 17/22* (2006.01)
(Continued)

(52) U.S. Cl.
CPC ....... *A46B 15/0012* (2013.01); *A46B 15/0044* (2013.01); *A46B 15/0081* (2013.01);
(Continued)

(58) Field of Classification Search
CPC ............ A46B 15/0012; A46B 15/0044; A46B 15/0081; A46D 3/00; A61C 17/16; A61C 17/2211; H05K 3/32
See application file for complete search history.

(56) References Cited

U.S. PATENT DOCUMENTS 5,815,872 A * 10/1998 Meginniss, III ... A46B 15/0002
15/105
5,876,207 A 3/1999 Sundius et al.
(Continued)

FOREIGN PATENT DOCUMENTS

GB 2473011 3/2011

OTHER PUBLICATIONS

International Search Report and the Written Opinion of the International Searching Authority issued in International Patent Application PCT/US2013/032762 mailed Sep. 16, 2013.
(Continued)

*Primary Examiner* — Shay Karls (57) ABSTRACT

A toothbrush having a pressure sensor. In one embodiment, the invention can comprise a body comprising a handle portion and a head portion having a basin; a cleaning assembly comprising: a head plate; a plurality of tooth cleaning elements, each of the plurality of tooth cleaning elements comprising a cleaning portion extending from a front surface of the head plate and a base portion extending from a rear surface of the head plate; the base portions of the plurality of tooth cleaning elements melted together to form a melt matte adjacent the rear surface of the head plate; the head plate of the cleaning element assembly positioned in the basin and connected to the head portion; a pressure sensor adjacent a rear surface of the melt matte; and an indicator operably coupled to the pressure sensor for gen-
(Continued)

erating a user perceptive signal upon the pressure sensor sensing a pressure that exceeds a predetermined threshold.

15 Claims, 5 Drawing Sheets

(51) Int. Cl.
*A46D 3/00* (2006.01)
*H05K 3/32* (2006.01)
*A61C 17/16* (2006.01)

(52) U.S. Cl.
CPC ............... *A46D 3/00* (2013.01); *A61C 17/16* (2013.01); *A61C 17/221* (2013.01); *H05K 3/32* (2013.01); *A46B 2200/1066* (2013.01); *Y10T 29/49131* (2015.01)

(56) References Cited

U.S. PATENT DOCUMENTS

| | | | |
|---|---|---|---|
| 6,327,734 | B1 | 12/2001 | Meginniss, III et al. |
| 6,389,636 | B1 | 5/2002 | Savill |
| 6,412,137 | B1 | 7/2002 | Heidari |
| 6,954,961 | B2 | 10/2005 | Ferber et al. |
| 7,774,891 | B2 * | 8/2010 | Pfenniger ............... A46B 3/06 15/167.1 |
| 2004/0060138 | A1 | 4/2004 | Pfenniger et al. |
| 2005/0091769 | A1 * | 5/2005 | Jimenez ................... A46B 3/20 15/22.1 |
| 2008/0276393 | A1 | 11/2008 | Russell et al. |
| 2010/0275397 | A1 | 11/2010 | Moskovich et al. |
| 2010/0325828 | A1 | 12/2010 | Braun et al. |
| 2011/0314677 | A1 | 12/2011 | Meier et al. |
| 2012/0171657 | A1 | 7/2012 | Ortins et al. |

OTHER PUBLICATIONS

Written Opinion of the International Preliminary Examining Authority issued in International Patent Application PCT/US2013/032762 mailed Nov. 24, 2014.

* cited by examiner

ORAL CARE IMPLEMENT HAVING PRESSURE SENSOR AND METHOD OF FORMING THE SAME

CROSS-REFERENCE TO RELATED PATENT APPLICATIONS

This application is a U.S. national stage application under 35 U.S.C. §371 of PCT Application No. PCT/US2013/032762, filed Mar. 18, 2013, which claims priority to Chinese Patent Application No. 201210596540.1, filed Dec. 21, 2012, the entireties of which are incorporated herein by reference.

BACKGROUND OF THE INVENTION

Daily toothbrushing has long been considered the most effective way to prevent the accumulation of bacteria on a person's teeth and gums. While toothbrushing is generally effective in cleaning the tooth surfaces, its effectiveness is greatly reduced if the force applied during brushing is inadequate. Furthermore, vigorous brushing of the teeth with excessive force can cause damage to a user's teeth and/or gum tissue. Thus, during an oral care session, a user may want to be alerted that they are brushing their teeth too hard.

Toothbrushes with pressure sensors of various types are known. However, known toothbrushes with pressure sensors are inadequate for several reasons. For example, some known toothbrushes with pressure sensors require an enlarged handle in order to accommodate the electrical circuitry required to alert a user as to the excessive brushing pressure. Other toothbrushes with pressure sensors require the incorporation of additional bulky structures in the head of the toothbrush in order to activate the pressure sensor. These known toothbrushes having pressure sensor devices can be expensive to manufacture and uncomfortable to use.

Therefore, a need exists for a toothbrush having a simplified pressure sensor mechanism that can easily alert the user that the user is brushing his or her teeth with excessive pressure.

BRIEF SUMMARY OF THE INVENTION

An oral care implement, such as a toothbrush, that comprises a pressure sensor and an indicator. The indicator is activated upon a pressure being applied to the pressure sensor that exceeds a predetermined threshold.

In one embodiment, the invention can be a toothbrush comprising: a body comprising a handle portion and a head portion, a basin formed into a front surface of the head portion; a cleaning assembly comprising: a head plate; a plurality of tooth cleaning elements, each of the plurality of tooth cleaning elements comprising a cleaning portion extending from a front surface of the head plate and a base portion extending from a rear surface of the head plate; the base portions of the plurality of tooth cleaning elements melted together to form a melt matte adjacent the rear surface of the head plate; the head plate of the cleaning element assembly positioned in the basin and connected to the head portion; a pressure sensor adjacent a rear surface of the melt matte such that pressure applied to the cleaning portions of the plurality of tooth cleaning elements is transmitted to the pressure sensor; and an indicator operably coupled to the pressure sensor for generating a user perceptive signal upon the pressure sensor sensing a pressure that exceeds a predetermined threshold.

In another embodiment, the invention can be a toothbrush comprising: a handle; a head; a plurality of tooth cleaning elements mounted to and extending from a front surface of the head; a printed circuit board located within the head, the printed circuit board having a front surface and a rear surface: a pressure sensitive switch attached to a front surface of the printed circuit board, wherein pressure applied to the plurality of tooth cleaning elements is transmitted to the pressure sensitive switch; and a light source attached to a rear surface of the printed circuit board, wherein the light source is illuminated upon the pressure sensitive switch closing in response to being subjected to a pressure that exceeds a predetermined threshold.

In yet another embodiment, the invention can be a method of forming a toothbrush comprising: a) forming a body comprising a handle portion and a head portion, a basin formed in a front surface of the head portion; b) operably coupling a light source to a rear surface of a printed circuit board and a pressure sensitive switch to a front surface of the printed circuit board, thereby forming a printed circuit board assembly; c) positioning the printed circuit board assembly within the basin; d) connecting a pre-formed cleaning element assembly to the head portion to enclose a front opening of the basin such that the pressure sensitive switch is responsive to pressure applied to a plurality of tooth cleaning elements of the pre-formed cleaning element assembly to activate the light source.

In still another embodiment, the invention can be a toothbrush comprising: a handle; a head; a plurality of tooth cleaning elements mounted to and extending from a front surface of the head; a printed circuit board located within the head, the printed circuit board having a front surface and a rear surface; a pressure sensor operably coupled to a front surface of the printed circuit board, wherein pressure applied to the plurality of tooth cleaning elements is transmitted to the pressure sensor; and a light source attached to a rear surface of the printed circuit board, wherein the light source is illuminated upon the pressure sensor being subjected to a pressure that exceeds a predetermined threshold.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 1:
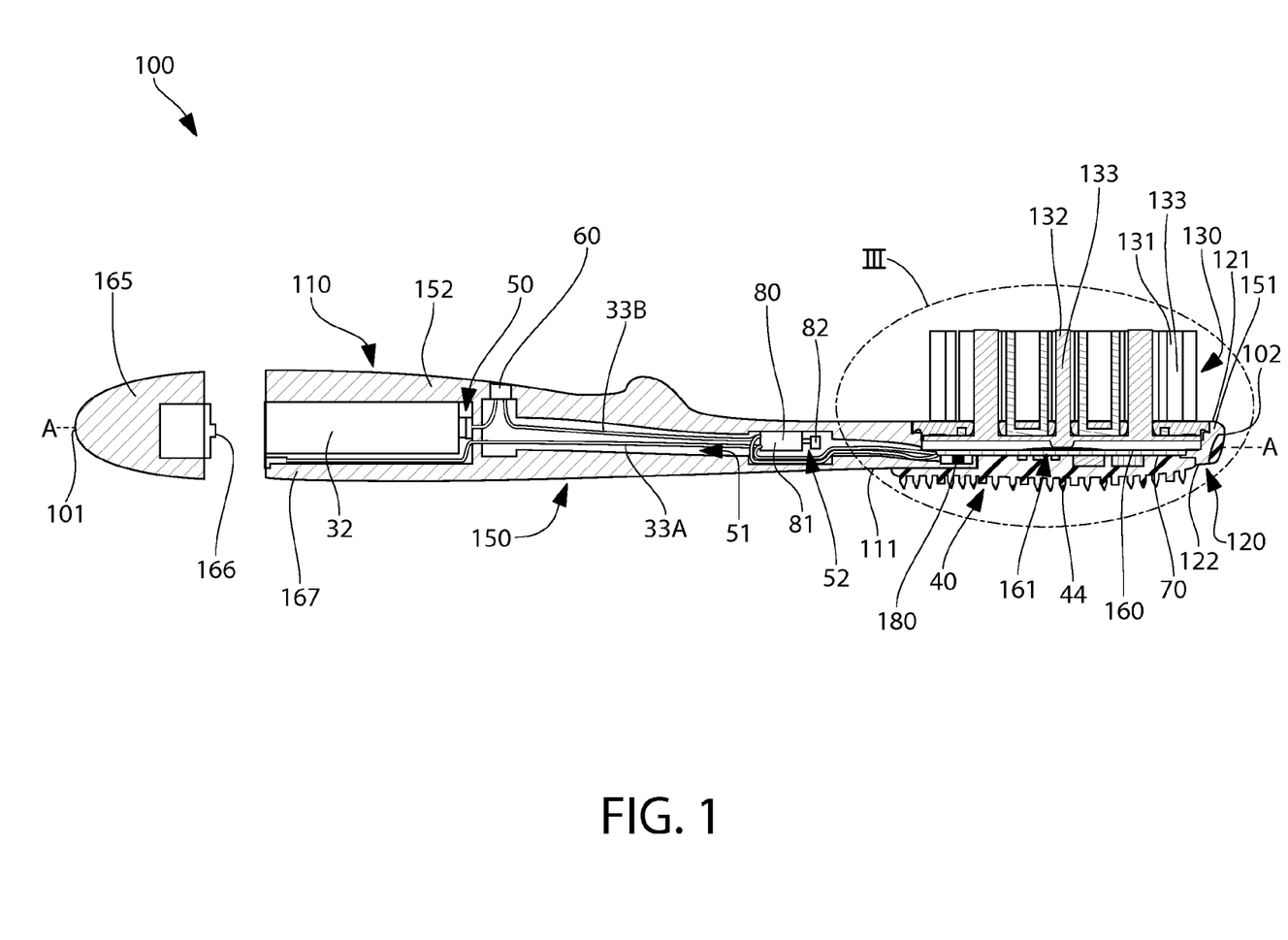
FIG. 1 is a longitudinal cross-sectional view of an oral care implement according to an embodiment of the present invention.
Figure 2:
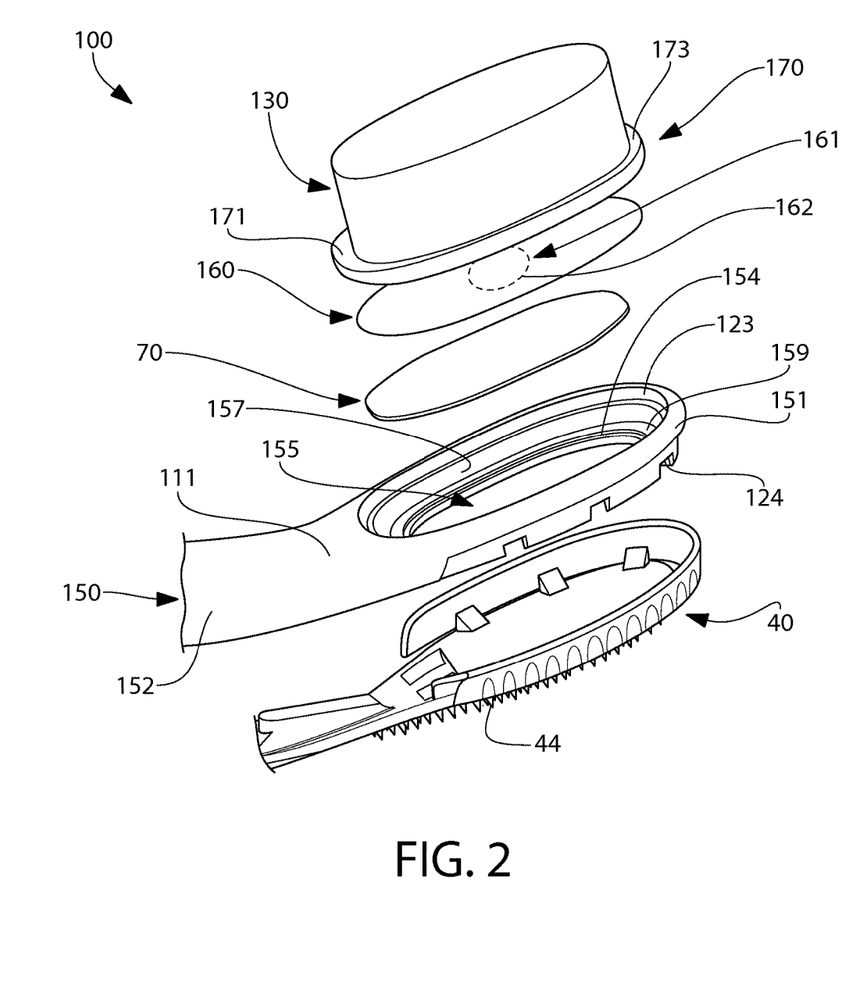
FIG. 2 is an exploded view of the head of the oral care implement of FIG. 1.
Figure 3:
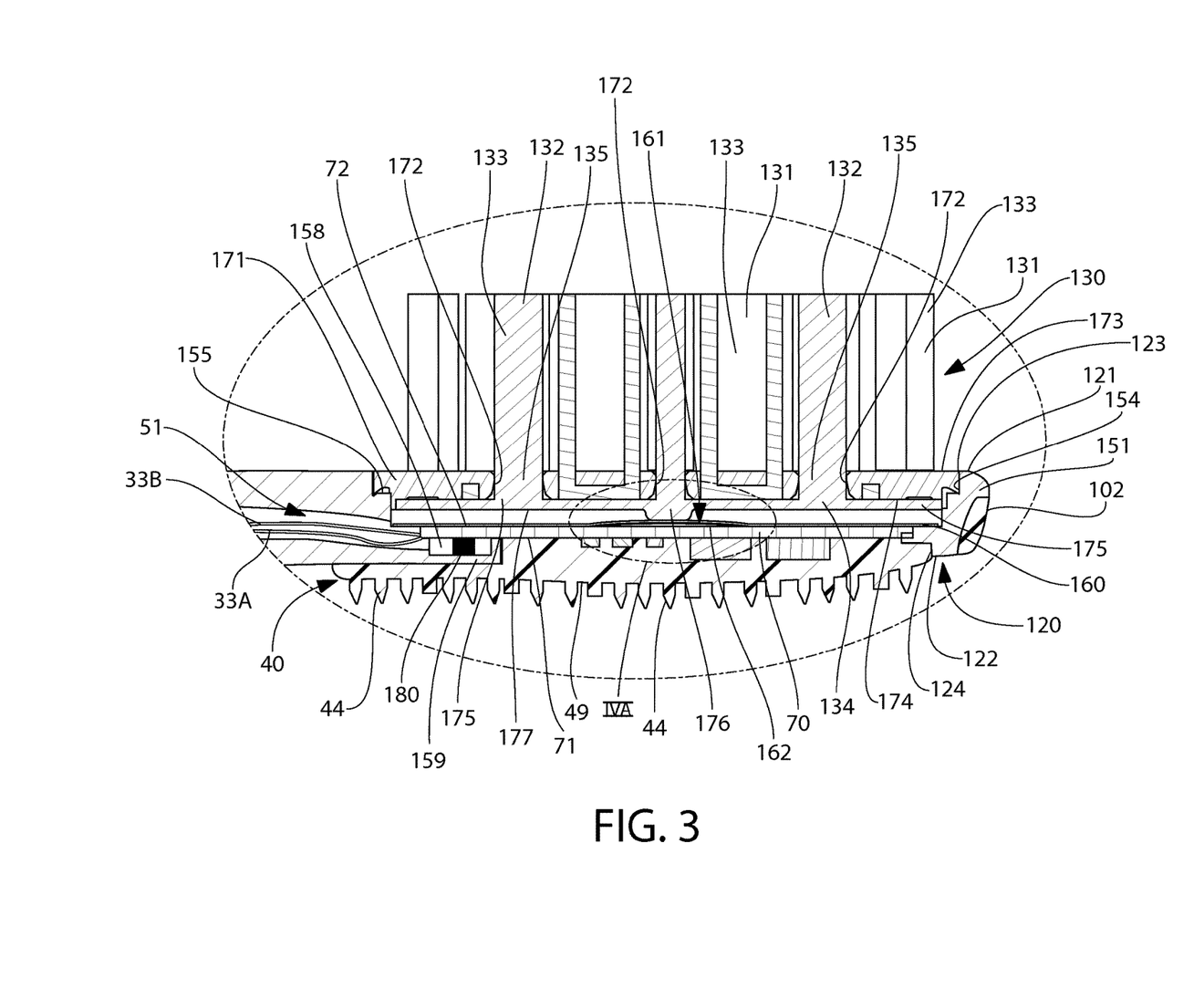
FIG. 3 is a close-up view of area III of FIG. 1.

Referring to FIGS. 1-3 concurrently, an oral care implement 100 according to an embodiment of the present invention is illustrated. While the oral care implement 100 is exemplified as a toothbrush, in other embodiments the oral care implement can take the form of a soft-tissue cleansing implement, an inter-proximal pick, a flossing tool, a plaque scraper, a powered toothbrush, or other ansate implement designed for oral care. It is also to be understood that other embodiments may be utilized, and that structural and functional modifications may be made without departing from the scope of the present invention.

The oral care implement 100 comprises a handle 110 and a head 120. The handle 110 provides the user with a mechanism by which he/she can readily grip and manipulate the oral care implement 100. The head 120 is connected to a distal end 111 of the handle 110 and includes a plurality of tooth cleaning elements 130 extending therefrom, which are generically illustrated. The oral care implement 100 extends from a proximal end 101 (which is also the proximal end of the handle 110) to a distal end 102 along a longitudinal axis A-A (illustrated in FIG. 1). Conceptually, the longitudinal axis A-A is a reference line that is generally coextensive with the three-dimensional center line of the handle 110 and the head 120. Because in certain embodiments the handle 110 is a non-linear structure, the longitudinal axis A-A for the oral care implement 100 is also non-linear in such embodiments. However, in certain other embodiments, the oral care implement 100 has a linear arrangement and, thus, has a substantially linear longitudinal axis A-A.

The oral care implement 100 comprises a body 150, which is the primary structural component of the oral care implement 100 to which the additional components are coupled or housed. The body 150 generally comprises a head portion 151 and a handle portion 152. The head portion 151 of the body 150 serves as the structural base for the head 120 of the oral care implement 100 while the handle portion 152 of the body 150 serves as the structural base for the handle 110 of the oral care implement 100. The body 150, in one embodiment, is constructed of a rigid material, such as for example a hard plastic. Suitable hard plastics include without limitation polyethylene, polypropylene (PP), polyamide, polyester, cellulosic, SAN, acrylic, ABS or any other of the commonly known thermoplastics used in toothbrush manufacture.

The head portion 151 is coupled to the handle portion 152 at the distal end 111 thereof (which is also the distal end 111 of the handle 110). In one embodiment, the head portion 151 and the handle portion 152 of the body 150 are formed as an integral structure using an injection molding process. In other embodiments, however, the handle portion 152 and the head portion 151 of the body 150 may be formed as separate components which are coupled together at a later stage of the manufacturing process by any suitable technique known in the art, including without limitation thermal welding, sonic welding, a tight-fit assembly, a coupling sleeve, adhesion, or fasteners. Whether the head portion 151 and the handle portion 152 are constructed as a single integral component or a multi-piece assembly (including connection techniques) is not limiting of the present invention in all embodiments, unless specifically recited in the claims. Furthermore, other manufacturing techniques may be used in place of and/or in addition to injection molding to create the body 150 (including the handle portion 151 and/or the head portion 152), such as milling and/or machining.

The head portion 151 of the oral care implement 100 comprises a front surface 121 and an opposing rear surface 122. A plurality of tooth cleaning elements 130 extend outwardly from the front surface 121 of the head portion 151. In certain embodiments, the plurality of tooth cleaning elements 130 may be mounted to and extend from the front surface 121 of the head 120. The body 150 of the oral care implement 100 comprises a basin 154 formed in the front surface 121 of the head portion 151. In the exemplified embodiment, the basin 154 forms a through-hole 155 in the head portion 151 of the body 150. However, in certain other embodiments the basin 154 may not extend completely through the head portion 151 and may instead have a floor that divides the basin 154 into a front basin and a rear basin, or that forms the rear surface 122 of the head portion 151. In such embodiments, the floor may be formed by a plate portion of the head portion 151 of the body 150.

In the exemplified embodiment wherein the basin 154 forms a through-hole 155, the through-hole 155 has a front opening 123 on the front surface 121 of the head portion 151 and a rear opening 124 on the rear surface 122 of the head portion 151. As a result of the through-hole 155, the head portion 151 is an annular structure. As will be discussed below, in the exemplified embodiment the basin 154 is provided to receive a portion of a cleaning assembly 170 when the plurality of cleaning elements 130 are mounted to the head portion 151 using, an anchor free tufting (AFT) technique.

In the exemplified embodiment, the head portion 151 comprises a ledge portion 159 that extends into the basin 154. In the exemplified embodiment, the ledge portion 159 is an annular extension of the inner surface 157 of the bead portion 151 that defines the basin 154. However, the invention is not to be so limited and the ledge portion 159 may be formed by opposing, linear extensions that extend inwardly towards the basin 154 from the inner surface 157 of the head portion 151. Alternatively, the ledge portion 159 may be formed by a plurality of spaced apart extensions extending inwardly towards the basin 154 from the inner surface 157 of the head portion 151. The ledge portion 159 provides a surface upon which components of the oral care implement 100 that are contained within the head portion 151 can rest. The structural arrangement of the ledge portion 159 and the components of the oral care implement 100 contained within the head portion 151 will be discussed in more detail below.

The plurality of tooth cleaning elements 130 are provided on the head 120 of the oral care implement 100 and extend from the front surface 121 of the head 120. The front surface 121 and the rear surface 122 of the head 120 can take on a wide variety of shapes and contours, none of which are limiting of the present invention. For example, the front and rear surfaces 121, 122 can be planar, contoured or combinations thereof. The front surface 121 and the rear surface 122 are bound by a peripheral or lateral surface.

The plurality of tooth cleaning elements 130 extend outward from the front surface 121 of the head 120 for cleaning, contact with teeth. Common examples of "tooth cleaning elements" include, without limitation, filament bristles, fiber bristles, nylon bristles, spiral bristles, rubber bristles, elastomeric protrusions, flexible polymer protrusions, co-extruded filaments, flag bristles, crimped bristles, anti-bacterial bristles and combinations thereof and/or structures containing such materials or combinations. In one embodiment, the plurality of tooth cleaning elements 130 comprises bristle tufts 131. In another embodiment, the plurality of tooth cleaning elements 130 comprises both bristle tufts 131 and elastomeric elements 132.

In certain embodiments of the invention, the plurality of tooth cleaning elements 130 can be connected to the head portion 151 of the body 150 in any manner known in the art. For example, in-mold tufting (IMT) or stapling techniques could be used to mount the plurality of tooth cleaning elements 130 to the head portion 151 of the body 150. Alternatively, the tooth cleaning elements 130 could be mounted to tuft blocks or sections by extending through suitable openings in the tuft blocks so that the base of the tooth cleaning elements 130 are mounted within or below the tuft block.

In the exemplified embodiment, the plurality of tooth cleaning elements 130 are coupled to the head portion 151 of the body 150 using an AFT mounting method by forming the tooth cleaning elements 130 on the cleaning assembly 170. The cleaning assembly 170 generally comprises a head plate 171 and the plurality of tooth cleaning elements 130 connected thereto. In AFT, the head plate 171 (which can be a membrane in certain embodiments) is formed haying a desired pattern of tuft holes 172 formed therein. The tuft holes 172 are holes that are formed through the head plate 171 from a front surface 173 of the head plate 171 to a rear surface 174 of the head plate 171. The tuft holes 172 can be thrilled through the head plate 171 in any desired pattern or configuration. As will be discussed below, the tooth cleaning elements 130 are coupled to the head plate 171 by inserting the tooth cleaning elements 130 into the tuft holes 172.

The head plate 171, in one embodiment, can be formed of an of the materials described above for the body 150. In one such embodiment, the head plate 171 is formed of one of the hard thermoplastics described above for the body 150 using an injection molding process. Once the head plate 171 is formed, one of the bristle tufts 131 (or other desired tooth cleaning element, such as an elastomeric element) is inserted into each of the tuft holes 172. When so inserted, a cleaning portion 133 of each of the bristle tufts 131 and elastomeric cleaning elements 132 (i.e., each of the plurality of tooth cleaning elements 130) protrudes from the front surface 173 of the head plate 171 while a base portion 134 of each of the bristle tufts 131 and elastomeric cleaning elements 132 (i.e., each of the plurality of tooth cleaning elements 130) protrudes from the rear surface 174 of the head plate 171. The cleaning portions 133 of the tooth cleaning elements 130 is the portion that contacts a users teeth during brushing whereas the base portions 134 of the tooth cleaning elements 130 remain beneath the head plate 171 and out of contact with the user's teeth during brushing. A central portion 135 of the tooth cleaning elements 130 is positioned within the tuft hole 172 and does not protrude from either of the front or rear surfaces 173, 174 of the head plate 171. As will be described in more detail below, the exact portion of the tooth cleaning elements 130 (i.e., the central portion 135) that is positioned within the tuft holes 172 can change because the tooth cleaning elements 130 are movable within the tuft holes 172.

After inserting the tooth cleaning elements 130 into the tuft holes 172 of the head plate 171 as described above, a heating element (such as a plate) is brought into contact with the base portions 134 of the tooth cleaning elements 130. The heating element melts the base portions 134 of the tooth cleaning elements 130, thereby fusing the base portions 134 together to form a melt matte 175 (also known as a bristle melt in the art). Alternatively, the base portions 134 of the tooth cleaning elements 130 can be melted by any means known for applying heat thereto, such as convective heated gas flow and/or irradiation.

When the melt matte 175 hardens, the plurality of tooth cleaning elements 130 are secured to the head plate 171 so that the tooth cleaning elements 130 cannot be pulled out though the front surface 173 of the head plate 171, thereby forming the cleaning assembly 170. Specifically, the melt matte 175 prevents the plurality of tooth cleaning elements 130 from being pulled through the tuft holes 172. However, the melt matte 175 is not affixed or otherwise connected to the rear surface 174 of the head plate 171 and the central portions 135 and cleaning portions 134 of the tooth cleaning elements 130 are not affixed or otherwise connected to the head plate 171 at the tuft holes 172. Rather, the melt matte 175 prevents the plurality of tooth cleaning elements 1130 from being pulled through the tuft holes 172 because the melt matte 175 forms a single mass of material that spans across a substantial entirety of the bottom surface 174 of the head plate 171. Thus, the single mass of material, that forms the melt matte 175 has a larger cross-sectional area than each individual tuft hole 172, and thus the melt matte 175 can not be pulled through the tuft holes 172. As a result, and because the melt matte 175 forms a portion of the tooth cleaning elements 130, the tooth cleaning elements 130 similarly can not be pulled through the tuft holes 172. Of course, in other embodiments the melt matte 175 may form several isolated melt mattes that are spaced from one another, however each of the melt mattes is larger than each individual tuft hole 172 to prevent pulling the tooth cleaning elements 130 through the tuft holes 172. While the process is described above using bristle tufts 131 and elastomeric cleaning elements 132, any type of tooth cleaning element 130 can be utilized to form the cleaning assembly 170 as described above instead of or in combination with the bristle tufts 131 and elastomeric cleaning elements 132.

As noted above, the melt matte 175 is not affixed or otherwise connected to the rear surface 174 of the head plate 171. As a result, the melt matte 175 (and hence also the tooth cleaning elements 130 which are integrally formed with the melt matte 175) can move relative to the head plate 171 in a direction transverse to the longitudinal axis A-A. Specifically, the melt matte 175 can move in opposing directions away from and back towards the rear surface 174 of the head plate 171 in response to forces being applied to the tooth cleaning elements 130. During use of the oral care implement 100, pressure applied to the cleaning portions 133 of the tooth cleaning elements 130 in a direction towards the front surface 173 of the head plate 171 will cause the melt matte 175 to move in a direction away from the rear surface 174 of the head plate 171. When pressure is no longer applied to the cleaning portions 133 of the tooth cleaning elements 130, the melt matte 175 is biased back into contact with the rear surface 174 of the head plate 171. Thus, as will be described in more detail below the melt matte 175 may come into contact with a pressure sensor during brushing to provide an indication to a user that he or she is brushing with too much force, and when the user is not brushing with too much force, the pressure sensor may bias the melt matte 175 back against the rear surface 174 of the head plate 171.

In the exemplified embodiment, the melt matte 175 is formed so as to include a protuberance 176 extending from a rear surface 177 of the melt mane 175. Of course, in certain other embodiments the protuberance 176 can be altogether omitted. The protuberance 176 can be formed by utilizing a heating element having a shape that corresponds to the desired shape of the melt matte 175 or by any other means such as pressing a shaping element against the melt matte 175 after heat is applied thereto. In the exemplified embodiment the protuberance 176 is a column-like protrusion extending from the rear surface 177 of the melt matte 175. However, the invention is not to be so limited in all embodiments and the shape of the protuberance 176 may take on any other form. The positioning and functionality of the protuberance 176, when such protuberance 176 is included in the melt matte 175, will be described in more detail below with reference to FIGS. 4A and 4B.

Once the cleaning assembly 170 is formed, the cleaning assembly 170 is aligned with the basin 154 in the head portion 151 of the body 150. The cleaning assembly 170 is then nested into the basin 154 (as shown in FIG. 3) and secured to the bead portion 151 of the body 150 so as to enclose the front opening 123 of the basin 154 (or the front opening 123 of the through-hole 155 when the basin 154 forms a through-hole). In one specific embodiment, the head plate 171 and the melt matte 175 are nested in the basin 154 so that the head plate 171 contacts an upper ledge 155 of the body 150. Once so positioned, the head plate 171 of the cleaning assembly 170 is secured to the head portion 151 using a technique such as thermal welding, sonic welding, or adhesion. Of course, other connection techniques can be utilized, such as snap-fit, tight-fit, etc.

Located within the basin 154 in the head portion 151 of the body 150 is the cleaning assembly 170, a pressure sensor 161, a seal layer 160 and a printed circuit board (PCB) 70. More specifically, the PCB 70 is positioned within the basin 154 so as to abut against the ledge portion 159. Thus, in the exemplified embodiment, the ledge portion 159 retains the PCB 70 properly within the basin 154. The invention is not to be so limited in all embodiments and in certain other embodiments the ledge portion 159 may be omitted and the PCB 70 can be retained in the basin 154 via a floor of the basin 154, or via an elastomeric material on a rear of the head.

In the exemplified embodiment, the pressure sensor 161 comprises a pressure sensitive switch 162 that is operably coupled to the PCB 70 and electrical contact elements that are attached to the PCB. In other embodiments, the pressure sensor 161 can be a transducer type pressure sensor that converts mechanical pressure into electrical energy, such as for example using a piezoelectric material. In still other embodiments, the pressure sensor 161 can take the form of one or more of the following: (1) a piezoresistive strain gauge that uses the piezoresistive effect of bonded or formed strain gauges to detect strain due to applied pressure; (2) a capacitive type pressure sensor that uses a diaphragm and pressure cavity to create a variable capacitor to detect strain due to applied pressure; (3) an electromagnetic pressure sensor that measures the displacement of a diaphragm by means of changes in inductance (reluctance), LVDT, Hall Effect, or by eddy current principle; (4) an optical pressure sensor that utilizes the use of the physical change of an optical fiber to detect strain due to applied pressure; (5) a potentiometric pressure sensor that uses the motion of a wiper along a resistive mechanism to detect the strain caused by applied pressure; (6) a resonant pressure sensor that uses the changes in resonant frequency in a sensing mechanism to measure stress, or changes in gas density, caused by applied pressure; (7) a thermal pressure sensor that uses the changes in thermal conductivity of a gas due to density changes to measure pressure (such as a Pirani gauge); and (8) an ionization pressure sensor that measures the flow of charged as particles (ions) which varies due to density changes to measure pressure.

Turning back to the exemplified embodiment, the pressure sensor 161 (or the pressure sensitive switch 162) is operably coupled to the PCB 70 and is positioned within the basin 154 so as to be adjacent the rear surface 174 of the melt matte 175. However, in the exemplified embodiment the pressure sensitive switch 162 is not in contact with the melt matte 175 due to the seal layer 160 being positioned between the pressure sensitive switch 162 and the melt matte 175. More specifically, the seal layer 160 is positioned between the PCB 70 and the melt matte 175 (and between the pressure sensor 161 and the melt matte 175) to protect the PCB 70 and the pressure sensor 161 from damage. As a result of the positioning of the pressure sensitive switch 162 of the pressure sensor 161, pressure applied to the cleaning portions 133 of the plurality of tooth cleaning elements 130 is transmitted to the pressure sensitive switch 162 of the pressure sensor 161 via the melt matte 175 as will be discussed in more detail below with reference to FIGS. 4A and 4B. The oral care implement 100 further comprises an indicator 180 operably coupled to the pressure sensor 161 for generating a user perceptive signal upon the pressure sensor 161 sensing a pressure that exceeds a predetermined threshold. As will be discussed in more detail below, the indicator 180 is operably coupled to the PCB 70 so that power is supplied to the indicator 180 when a user is brushing his or her teeth with a force that exceeds a predetermined threshold.

In the exemplified embodiment, the indicator 180 is a light source. However, the invention is not to be limited to the indicator 180 being a light source in all embodiments and the indicator 180 can be any device capable of signifying a condition to a user. Thus, in certain other embodiments the indicator 180 can be an audio source or speaker, a vibratory element, or the like. Thus, although portions of the description below make reference to a "light source 180," it should be understood that any other type of indicator can be used in lieu of a light source. Thus, the invention is not to be specifically limited, to the indicator being, a light source unless a light source is specifically recited in the claims.

In the exemplified embodiment wherein the indicator 180 is a light source, the light source is a light emitting diode (LED). However, in other embodiments, the light source can be a bulb or other light emitting device as is known in the art. The light source (i.e., the indicator 180) is operably coupled to the PCB 70 in the exemplified embodiment. More specifically, in the exemplified embodiment the light source is attached to a rear surface 71 of the PCB. The PCB 70 acts as a foundational substrate for the light source and includes the required electrical circuitry and components required to illuminate the light source when power is supplied from a power source 32 to the PCB 70 via electrical wires 33A-B. In the exemplified embodiment, the PCB 70 is a unitary structure that is formed of a rigid material to which electrical components can be attached in order to provide power to those components.

As noted above, the PCB 70 is positioned within the basin 154 so as to rest on and abut against the ledge portion 159. In the exemplified embodiment, a depression 158 is formed into the ledge portion 159 in order to accommodate the light source (i.e., indicator 180). Thus, when the PCB 70 is positioned within the basin 154 and the light source is attached to the rear surface 71 of the PCB 70, the light source nests within the depression 158 formed into the ledge portion 159 of the head portion 151. Although in the exemplified embodiment the light source is positioned within the head portion 151 of the oral care implement 100, the invention is not to he so limited in all embodiments and in certain other embodiments the light source can be otherwise positioned on the oral care implement, such as in the handle portion 152 or in an end cap 165 (FIG. 1) as will be discussed in more detail below.

The head 120 extends along a longitudinal axis from a proximal end of the head 120 (adjacent the handle 110) to a distal end of the head 120. Furthermore, in the exemplified embodiment the light source 180 is positioned so that a first transverse axis or plane that is substantially perpendicular to the longitudinal axis of the head 120 (which in certain embodiments may be the longitudinal axis A-A) intersects both the light source 180 and at least one of the plurality of tooth cleaning elements 130. Thus, in the exemplified embodiment the light source 180 is positioned beneath the tooth cleaning elements 130 and at a location such that a transverse axis or plane intersects the light source 180 and at least one of the plurality of tooth cleaning elements 130. Furthermore, the pressure sensitive switch 162 is positioned so that a second transverse axis or plane that is substantially perpendicular to the longitudinal axis of the head 120 intersects both the pressure sensitive switch 162 and at least one of the plurality of tooth cleaning elements 130. In the exemplified embodiment, the second transverse axis or plane is oriented, substantially parallel to the first transverse axis plane. Furthermore, in the exemplified embodiment the first and second transverse axes or planes are axially offset from one another along the longitudinal axis A-A. However, the invention is not to be so limited and in certain other embodiments the same transverse plane may intersect both the light source 180 and the pressure sensitive switch 162 (thus, the light source 180 and the pressure sensitive switch 162 may be axially aligned).

As noted above, the pressure sensor 161 comprises a pressure sensitive switch 162 that is operably coupled to the PCB 70 and electrical contact elements that are attached to the PCB 70. In the exemplified embodiment, the pressure sensitive switch 162 is a metal-dome switch. However, the invention is not to be so limited in all embodiments and the pressure sensitive switch 162 can be any other type of switch. As will be understood from the description below, in the exemplified embodiment the pressure sensitive switch 162 is a force activated dome switch that detects the push force that acts directly on the tooth cleaning elements 130 in order to detect when a user is brushing with a force that exceeds a predetermined threshold.

In certain embodiments, the pressure sensitive switch 162 can be considered attached to or mounted on a front surface 72 of the PCB 70. Thus, in certain embodiments the pressure sensitive switch 162 is attached to the front surface 72 of the PCB 70 and the indicator 180 (i.e., light source) is attached to the rear surface 71 of the PCB 70. This enables all of the electrical components to easily fit within the basin 154 in the head portion 151. However, in other embodiments the pressure sensitive switch 162 is merely operably coupled to the PCB 70 rather than directly attached to the PCB 70. In such embodiments, the pressure sensitive switch 162 comes into and out of contact with the PCB 70 to open and close the switch. Thus, the pressure sensitive switch 162 can be separate and isolated from the PCB 70 when the switch is in the open position, and the pressure sensitive switch 162 can come into contact with the PCB 70 (or specifically the electrical contact elements on the PCB 70) when the switch is in the closed position. In the exemplified embodiment, the pressure sensitive switch 162 is a dome-shaped component in its biased form, and pressure applied to the tooth cleaning elements 130 causes the pressure sensitive switch 162 to flatten out so as to contact the electrical contact elements. In the exemplified embodiment, the pressure sensitive switch 162 is formed of metal so that the pressure sensitive switch 162 can be used to close a circuit between two electrical contact elements. Pressure applied to the pressure sensitive switch 162 causes the pressure sensitive switch 162 to move downwardly as illustrated in FIG. 4B and discussed in more detail below.

The electrical contact elements on the PCB 70 are spaced from one another and in the biased form of the pressure sensitive switch 162, current does not flow between the electrical contact elements. Thus, when the pressure sensitive switch 162 is in its biased form, a circuit providing power to the indicator 180 is in an open position such that current is unable to flow into the indicator 180 to provide power to the indicator 180. Upon the pressure sensitive switch 162 being forced into contact with both of the electrical contact elements, the circuit providing power to the indicator 180 is closed and the indicator 180 becomes powered.

The pressure sensitive switch 162 is biased into an open position such that the pressure sensitive switch 162 is not in contact with at least one of the electrical contact elements. When pressure that exceeds a predetermined threshold (i.e., that exceeds the bias) is applied to the tooth cleaning elements 130, the melt matte 175 will contact the pressure sensitive switch 162 and cause the pressure sensitive switch 162 to be placed into a closed position whereby the pressure sensitive switch 162 is in contact with both of the electrical contact elements. When the pressure sensitive switch 162 is forced into the closed position, the indicator 180 will be actuated such as by illuminating a light source, emitting sound from a speaker, vibrating a vibratory element, or the like.

The seal layer 160 is positioned within the basin 154 so as to rest atop of the PCB 70 and the pressure sensor 161. Thus, the seal layer 160 is positioned in between the PCB 70/pressure sensor 161 and the melt matte 175. As a result, the seal layer 160 seals a front surface 72 of the PCB 70 and the pressure sensor 161 to protect the PCB 70 and the pressure sensor 161 against water or other damage during use of the oral care implement 100. The seal layer 160 can be formed of any desired material, such as a thermoplastic, thermoset, rubber, or other material used for sealing surfaces sufficient to create a seal to prevent the ingress of water onto the PCB 70 and other electrical components. The seal layer 160, in one embodiment, is formed of a thermoplastic elastomer, such as those described below for the light transmissive elastomeric material 40. The seal layer 160 seals the front surface 35 of the PCB 70 so that moisture that may be introduced into the head portion 151 is prohibited from contacting the PCB 70. In certain embodiments, the seal layer 160 may also form a seal with the head portion 151 of the body 150. In certain embodiments, however, the seal layer 460 may be omitted if desired.

The handle portion 152 of the body 150 further comprises a cavity 50 in which a power source 32 is located. The power source 32 is operably coupled to the PCB 70 to provide power to the indicator 180. In the exemplified embodiment, the power source 32 is operably coupled to the PCB 70 via wires 33A, 33B. The wires 33A, 33B extend through an internal longitudinal passageway 51 that extends through the handle portion 152. More specifically, the passageway 51 extends from the cavity 50 and terminates at the basin 154 or through-hole 155 in the head portion 151. The power source 32, in the exemplified embodiment, is a replaceable battery. Of course, in other embodiments the power source can be a rechargeable battery, a photovoltaic cell, or any other device capable of generating a suitable amount of electricity to power the indicator 180. In one embodiment, the power source 32 can be an electro-dynamic cell that is charged by the mechanical action of the oral care implement 100 during use.

An actuator 60, in the form of an off/on button, is provided in operable coupling between the power source 32 and the indicator 180 so that a user can control whether or not to provide power to the indicator 180 to facilitate proper operation of the indicator 180. The actuator 60 can be a slide button, a push button, a capacitive touch sensor, or any other type of actuator known in the art. The handle portion 152 of the body 150, in the exemplified embodiment, also comprises an end cap 165 that can be detachably coupled to a main body portion 167 of the handle portion 152 so that the power source 32 can be removed and/or replaced as necessary. An electrical contact 166 is provided on the end cap 165 so that upon the end cap 165 being coupled to the main body portion 167, the electrical circuit is complete and the indicator 180 can be powered on and off by manipulation of the actuator 60 (and by the pressure sensitive switch 162 of the pressure sensor 161 being closed). In certain embodiments, the indicator 180 or light source may be an LED or other type of light that is disposed within the end cap 165 so that the end cap 165 illuminates when a user brushes his or her teeth with a pressure that exceeds a predetermined threshold. Alternatively, the indicator 180 can be an audio device, speaker, vibratory element or the like that is located within the end cap 165 (as opposed to being located in the head 120).

In certain embodiments, such as the exemplified one, the oral care implement 100 further comprise a motion inducing element 80 for imparting motion to the head 120 of the oral care implement 100. The motion inducing element 80, in the exemplified embodiment, comprises a motor 81 and an eccentric 82 that is driven by the motor 81 to create vibrations that are transmitted to the head 120 of the oral care implement 100. Of course, other motion inducing elements can be used, including motor and drive coupling assemblies that move one or more tuft blocks on the head 120. The motion inducing element 80 is housed in a chamber 52 located within a thinned neck portion of the handle portion 152.

The motion inducing element 80 is operably coupled to the wires 33A, 33B and is powered by the power source 32. The motion inducing element 80 can be wired in series or in parallel with the indicator 180. Furthermore, in certain embodiments, the electrical circuit is designed so that: (1) the indicator 180 can be turned on independent of the motion inducing element 80 and vice versa by selective positioning of the actuator 60; and/or (2) the indicator 180 and motion inducing element 80 can be turned on concurrently. As will be better understood from the discussion of FIGS. 4A and 4B, in certain embodiments the indicator 180 is only turned on when the pressure sensor 161, which comprises the pressure sensitive switch 162, is in the closed position such that current can flow through the pressure sensitive switch 162, regardless of the positioning of the actuator 60.

As noted above, the cleaning assembly 170, the seal layer 160, the pressure sensor 161 and the PCB 70 are located within the through-hole 155 (or the basin 154) in a stacked assembly. Furthermore, a light transmissive elastomeric material 40 is coupled to the head portion 151 so as to enclose the rear opening 124 of the through-hole 155 and seal the rear surface 71 of the PCB 70. In one embodiment, the light transmissive elastomeric material 40 is transparent. In another embodiment, the light transmissive elastomeric material 40 is translucent. Suitable materials for forming the light transmissive elastomeric material 40 include any biocompatible resilient material suitable for uses in an oral hygiene apparatus, such as thermoplastic elastomer. To provide optimum comfort as well as cleaning benefits, the light transmissive elastomeric material 40 preferably has a hardness property in the range of A8 to A25 Shore hardness. As an example, one preferred elastomeric material is styrene-ethylene/butylene-styrene block copolymer (SEBS) manufactured by GLS Corporation. Nevertheless, SEBS material from other manufacturers or other materials within and outside the noted hardness range could be used.

In certain embodiments, light refractive particles can be included in the light transmissive elastomeric material 40 to provide enhanced dispersion of light through and from the light transmissive elastomeric material 40 during use. In one embodiment in which a TPE is used to create the light transmissive elastomeric material 40, the light transmissive elastomeric material 40 can be coupled to the body 150 by overmolding the light transmissive elastomeric material 40 to the body 150 in the appropriate shape.

In one embodiment, the light transmissive elastomeric material 40 is a single unitary mass that is formed integrally, using a technique such as injection molding. In other embodiments, the light transmissive elastomeric material 40 may be formed of other materials. For example, in one embodiment, the light transmissive elastomeric material 40 can be formed of a light transmissive thermoplastic, including transparent or translucent hard plastics. Suitable light transmissive hard plastics include, without limitation, transparent or translucent versions of polyethylene, polypropylene (PP), poly amide, polyester, cellulosic, SAN, acrylic, ABS or any other of the commonly known thermoplastics used in toothbrush manufacture. In one such embodiment, the light transmissive elastomeric material 40 is integrally formed with the body 150 and, thus, would be considered as being "coupled to the body 150" during the formation process of the body 150, which can be an injection molding process. In still other embodiments, the light transmissive elastomeric material 40 can comprise fiber optics, crystalline materials, or any other material or combination of materials capable of distributing light. In embodiments of the invention, the light transmissive elastomeric material 40 can be coupled to the body 150 by adhesion, thermal coupling, sonic welding, overmolding, a snap-fit assembly, a tight-fit assembly, combinations thereof, or other connection techniques that would be known to those of skill in the art. The exact coupling technique will depend on the material of construction of the light transmissive elastomeric material 40 and the body 150.

As discussed above, in the exemplified embodiment the indicator 180 is positioned within a depression 158 that is formed into the ledge portion 159. However, in other embodiments the indicator or light source 180 can be embedded into the light transmissive elastomeric material 40 such that the depression 158 ma be omitted. Thus, the light transmissive elastomeric material 40 itself may be used to maintain the PCB 70 and the indicator 180 in the desired position within the basin 154. Regardless, the light transmissive elastomeric material 40 is coupled to the head portion 151 so as to overly the light source 180. As a result, and due to the material of the light transmissive elastomeric material 40, light from the light source 180 (when the light, is generated by closing the pressure sensitive switch 162) is able to penetrate through the light transmissive elastomeric material 40 so as to be visible to a user. In other embodiments, the light that is generated by the light source 180 merely lights up the light transmissive elastomeric material 40 in a manner that it is decipherable to a user. As will be discussed in more detail below with regard to FIG. 5, in the exemplified embodiment light from the light source 180 is visible through a neck portion of the oral care implement 100. This is possible although the light source 180 is located within the head portion 120 and adjacent to the neck because the light generated from the light source 180 is distributed along the light transmissive elastomeric material 40.

Figure 5:
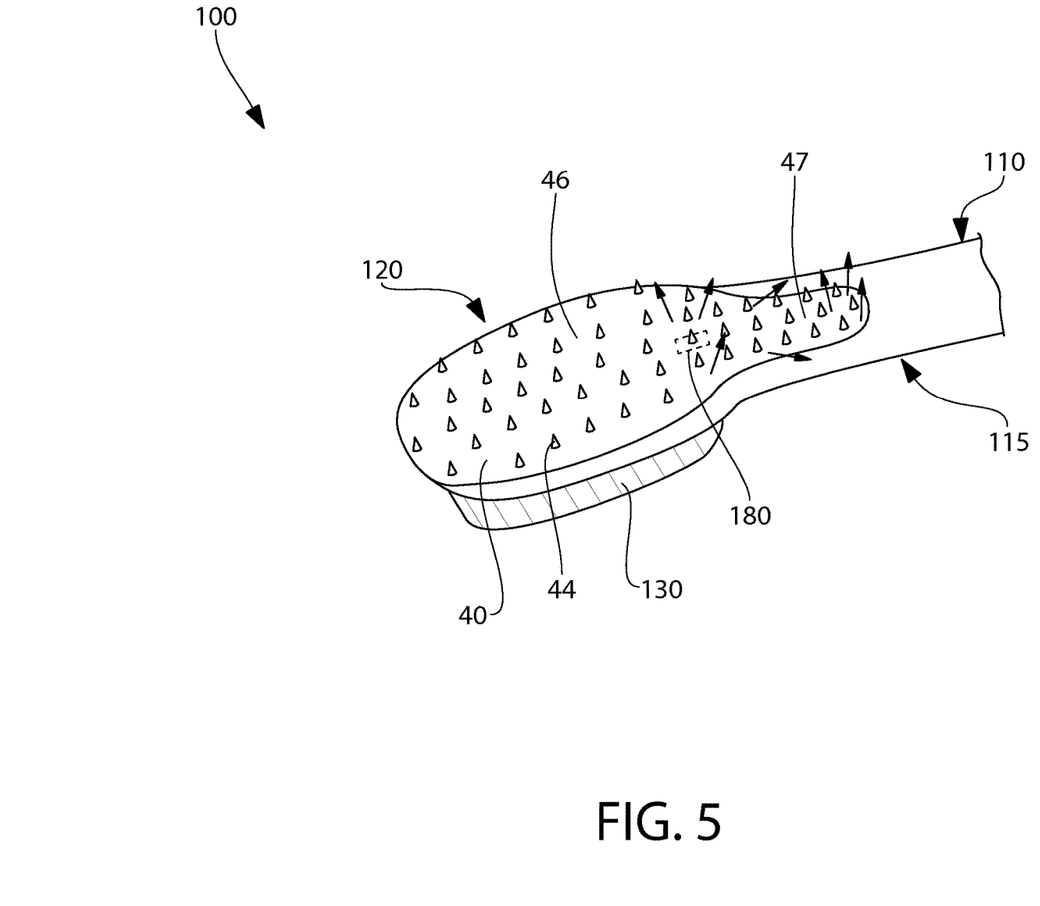
FIG. 5 is a rear perspective view of the head of the oral care implement of FIG. 1.

In the exemplified embodiment, the light transmissive elastomeric material 40 further comprises a plurality of protuberances 44 extending from an outer surface 49 of the light transmissive elastomeric material 40. The plurality of protuberances 44 extend beyond the rear surface 122 of the head portion 151 of the oral care implement 100. The plurality of protuberances 44 are provided so that the light transmissive elastomeric material 40 can also be used to cleanse soft tissue. In the exemplified embodiment, the plurality of protuberances 44 are nubs. In one embodiment, the plurality of protuberances 44 are conical nubs. As used herein a "nub" is generally meant to include a column-like protrusion without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection). The base width can be substantially larger than the height.

The plurality of protuberances 44 are designed to significantly reduce a major source of bad breath in people and improve hygiene. The plurality of protuberances 44 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, the plurality of protuberances 44 provide for gentle engagement with the soft tissue while reaching downward into the recesses of adjacent papillae of the tongue. In other embodiments, the plurality of protuberances 44 can take the form of ribs, flaps, ridges, raise edges, or combinations thereof.

Figure 4A:
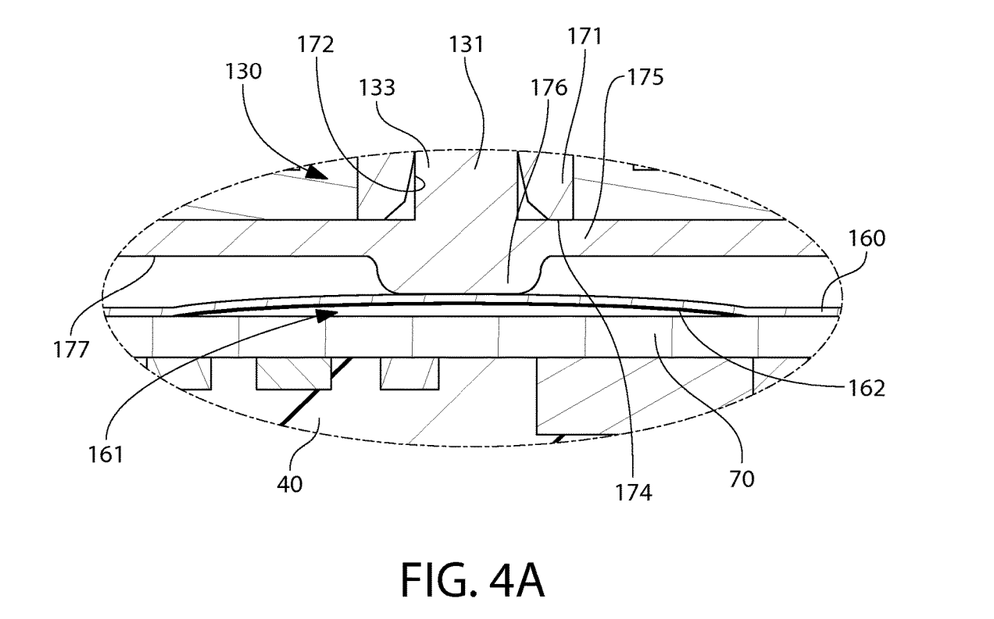
FIG. 4A is a close-up view of area IVA of FIG. 3, wherein no pressure is being applied to cleaning portions of tooth cleaning elements and a pressure sensitive switch is in an open position.
Figure 4B:
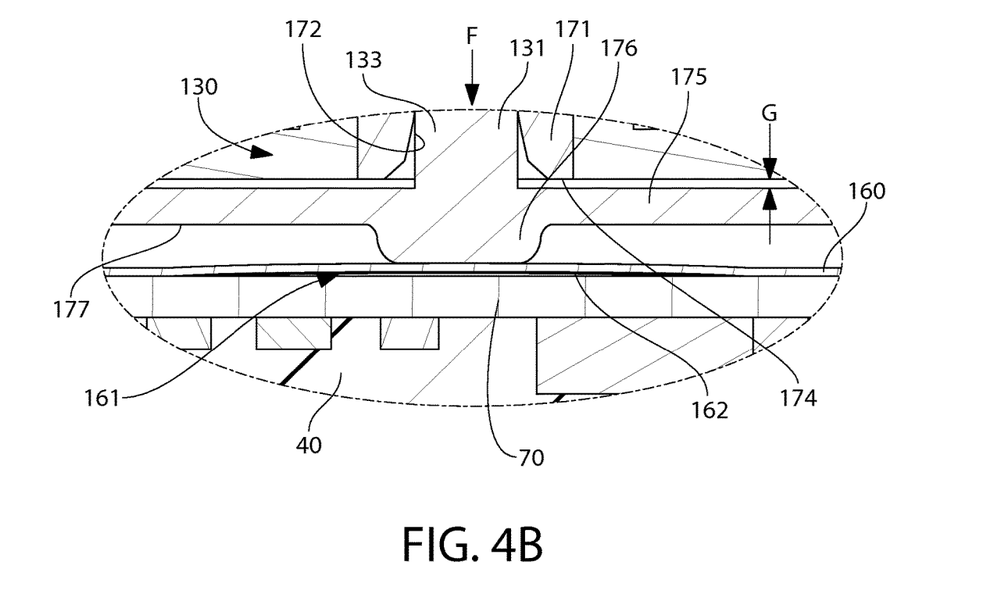
FIG. 4B is the close-up of FIG. 4A, wherein pressure is being applied to the cleaning portions of the tooth cleaning elements and the pressure s is in a closed position.

Referring now to FIGS. 4A and 4B, operation of the pressure sensor 161 will be described. In FIG. 4A, the pressure sensitive switch 162 of the pressure sensor 161 is in its biased position whereby no pressure is being applied to the tooth cleaning elements 130. In its biased position, the pressure sensitive switch 162 in the exemplified embodiment has a dome shape. The pressure sensitive switch 162 of the pressure sensor 161 is biased into the open position. In the open position, the pressure sensitive switch 162 is spaced from the PCB 70, and more specifically spaced front at least one electrical contact element on the PCB 70. Furthermore, in the open position the melt matte 175 is in contact with the rear surface 174 of the head plate 171 such that no pressure is applied from the melt matte 175 onto the pressure sensitive switch 162. In certain embodiments, in the biased open position, the pressure sensitive switch 162 is spaced from both of the electrical contact elements and in other embodiments the pressure sensitive switch 162 is always in contact with one of the electrical contact elements, and only comes into contact with a second of the electrical contact elements upon application of a force to the cleaning portions 133 of the cleaning elements 130. When the pressure sensitive switch 162 is in the open position, a circuit between the power source 32 and the indicator 180 is open and no power is provided to the indicator 180.

Referring, to FIG. 4B, the pressure sensitive switch 162 is illustrated in a closed position, which is achieved by application of a force F being applied to the cleaning portions 133 of the tooth cleaning elements 130. Specifically, upon the force F being applied to the cleaning portions 133 of the tooth cleaning elements 130, the force F is transmitted to the pressure sensitive switch 162 so as to force the pressure sensitive switch into the closed position. The force F is a force or pressure that exceeds a predetermined threshold. Specifically, the force F or pressure is a predetermined amount of force or pressure that is known to be detrimental when applied to a user's teeth during tooth brushing. In certain embodiments, the force F is between 3.5-4.5 Newtons, more preferably between 3.8-4.2 Newtons, and still more preferably approximately 4 Newtons.

Thus, upon the force F exceeding the predetermined threshold, the melt matte 175 moves downwardly and presses the pressure sensitive switch 162 downwardly in the direction of the rear surface 122 of the head 120, thereby closing the space between the pressure sensitive switch 162 and the PCB 70. In the exemplified embodiment the seal layer 160 is located between the melt matte 175 and the pressure sensitive switch 162 such that the melt matte 175 contacts the seal layer 160, which in turn moves the pressure sensitive switch 162 downwardly as described herein. The force F being applied to the cleaning portions 133 of the tooth cleaning elements 130 causes the pressure sensitive switch 162 to flatten out from its biased dome shape. When the force F exceeds the predetermined threshold, the pressure sensitive switch 162 moves into contact with both of the electrical contact elements on the PCB 70, thereby closing the circuit. As discussed above, in the exemplified embodiment the pressure sensitive switch 162 is formed of metal, which enables current to flow through the pressure sensitive switch 162 when the pressure sensitive switch 162 is in the closed position. However, the invention is not to be so limited and the pressure sensitive switch 162 can be formed of any type of material that conducts electricity. When the force F is applied to the cleaning portions 133 of the tooth cleaning elements 130, the melt matte 175 moves in a downward direction away from the rear surface 174 of the head plate 171. Thus, the force F applied to the cleaning portions 133 of the tooth cleaning elements 130 causes a gap G to be formed between the melt matte 175 and the rear surface 174 of the head plate 171.

In the exemplified embodiment, it is the protuberance 176 of the melt matte 175 that comes into contact with the pressure sensitive switch 162 (via the seal layer 160) when the force F is applied to the cleaning portions 133 of the tooth cleaning elements 130. Thus, in embodiments that comprise the protuberance 176 (such as the exemplified embodiment), the protuberance actuates the pressure sensitive switch 162 during use of the oral care implement 100. In certain embodiments the protuberance 176 can be omitted and the rear surface 177 of the melt matte 175 can be used to actuate the pressure sensitive switch 162.

As a result of the pressure sensitive switch 162 contacting both of the electrical contact elements on the PCB 70, and due to the operable connection between the power source 32, the indicator 180 and the PCB 70, power is supplied from the power source 32 to the indicator 180 so that the indicator 180 as activated. Activation of the indicator 180 can result in the indicator generating light (when the indicator is a light source), emitting a sound (when the indicator is a speaker), or vibrating (when the indicator is a vibratory element).

During use of the oral care implement, when a user is brushing with a force F that exceeds the predetermined threshold, the indicator 180 will activate to provide an indication to the user that he or she is brushing with too much force. Thus, upon the indicator 180 activating, the use will reduce the amount of brushing force being used until the indicator 180 deactives (such as by the light source turning off). The user can complete this action without ever stopping the toothbrushing action. Upon the user decreasing the brushing force, the pressure sensitive switch 162 will bias back into its dome shape, thereby biasing the melt matte 175 back into contact with the bottom surface 174 of the head plate 171 as illustrated in FIG. 4A.

In certain embodiments, the pressure sensitive switch 162 can be omitted and the protuberance 176 can include a metal or other conductive material on its bottom surface. Specifically the bottom surface of the protuberance 176 can be coated with a conductive material. In such embodiments, the protuberance 176 can be used as the switch such that the protuberance 176 coming into contact with the PCB 70 (and the electrical contact elements thereon) will close the switch and enable current to flow from the power source 32 to the indicator 180. In such embodiments, the seal layer 160 will have an opening therein for the protuberance 176 to extend through the seal layer 160 for contact with the PCB 70. The seal layer 160 may be secured directly to the melt matte 175 to prevent the ingress of fluids onto the PCB 70. In other embodiments, the rear surface 177 of the melt matte 175 can be coated with the conductive material to form the switch.

Referring now to FIG. 5, a rear perspective view of the head 120 and a neck portion 115 of the handle 110 of the oral care implement 100 is illustrated. The head 120 of the oral care implement 100 has the tooth cleaning elements 130 extending from the front surface thereof, and the light transmissive elastomeric material 40 with protuberances 44 extending therefrom on a rear surface thereof. The light transmissive elastomeric material 40 comprises a first portion 46 that overlies the rear surface of the head 120 including the indicator 180 (i.e., light source) and a second portion 47 that overlies the neck portion 115 of the handle 110. Despite the indicator or light source 180 being located on the head 120, light generated by the light source 180 is distributed by the light transmissive elastomeric material 40 form the first portion 46 to the second portion 47. As a result, the light from the light source 180 is transmitted through the light transmissive elastomeric material 40 at the neck portion 115 of the oral care implement 100. This enables the light to be visible to a user even during brushing. Specifically, during brushing the head 120 of the oral care implement 100 is located within the user's mouth, and therefore light emitting through the head 120 may not be visible to the user. However, the neck portion 115 of the oral care implement 100 is not entirely contained within the user's mouth during brushing. Thus, when the light emits through the neck portion 115, the user can see the light. As a result, when the light emits via the neck portion 115 of the oral care implement 100, the user will be informed that the user is brushing with excessive force.

In order to ensure that the light emits through the neck portion 115, the first portion 46 of the light transmissive elastomeric material 40 can be formed of a higher density than the second portion 47 of the light transmissive elastomeric material 40. Alternatively, the first portion 46 of the light transmissive elastomeric material 40 can be formed of a material that is less light transmissive than the second portion 47 of the light transmissive elastomeric material 40. Still further, a reflector can be positioned between the light source 180 and the first portion 46 of the light transmissive elastomeric material 40 to reflect the light towards the second portion 47 of the light transmissive elastomeric material. Any of these arrangements will ensure that the light generated by the light source 180 emits through the neck portion 115 of the oral care implement 100.

Referring to FIGS. 1-5 concurrently, in one embodiment the invention can be directed to a method of forming a toothbrush as described herein above. In such an embodiment, the invention comprises forming the body 150 comprising the handle portion 152 and the head portion 151, with the basin 154 formed into the front surface 121 of the head portion 151. The method then comprises operably coupling the light source 180 to the rear surface 71 of the PCB 70 and operably coupling the pressure sensitive switch 162 to the front surface 72 of the PCB 70, thereby forming a printed circuit board assembly. Next, the method includes positioning, the PCB 70 within the basin 154 and connecting the pie-formed cleaning element assembly 170 to the head portion 151 to enclose the front opening 123 of the basin 154 such that the pressure sensitive switch 162 is responsive to pressure applied to a plurality of tooth cleaning elements of the pre-formed cleaning element assembly 170 to activate the light source 180.

In certain embodiments, the pre-formed cleaning element assembly 170 is formed prior to connecting the pre-formed cleaning element assembly 170 to the head portion 151. In such embodiments, the pre-formed cleaning element assembly 170 is formed by inserting the plurality of tooth cleaning elements 130 through the tuft holes 172 in the head plate 171 so that each of the plurality of tooth cleaning elements 130 comprises the cleaning portion 133 extending from the front surface 173 of the head plate 171 and the base portion 134 extending from the rear surface 174 of the head plate 171. Finally, forming the pre-formed cleaning element assembly 170 comprises melting the base portions 134 of the plurality of tooth cleaning elements 130 to form the melt matte 175 adjacent to the rear surface 174 of the head plate 171.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A toothbrush comprising:
   a body comprising a handle portion and a head portion, a basin formed into a front surface of the head portion;
   a cleaning assembly comprising:
      a head plate; and
      a plurality of tooth cleaning elements, each of the plurality of tooth cleaning elements comprising a cleaning portion extending from a front surface of the head plate and a base portion extending from a rear surface of the head plate;
      the base portions of the plurality of tooth cleaning elements melted together to form a melt matte;
      the head plate of the cleaning element assembly positioned in the basin and non-movably connected to the head portion;
   a pressure sensor adjacent a rear surface of the melt matte, the melt matte movable within the basin such that pressure applied to the cleaning portions of the plurality of tooth cleaning elements is transmitted to the pressure sensor via contact between the melt matte and the pressure sensor; and
   an indicator operably coupled to the pressure sensor for generating a user perceptive signal upon the pressure sensor sensing a pressure that exceeds a predetermined threshold.

2. The toothbrush according to claim 1 further comprising a printed circuit board located within the basin, wherein the pressure sensor comprises a pressure sensitive switch operably coupled to the printed circuit board, and wherein the indicator is operably coupled to the printed circuit board.

3. The toothbrush according to claim 2 wherein the printed circuit board comprises a front surface and a rear surface, the pressure sensitive switch attached to the front surface of the printed circuit board and the indicator attached to the rear surface of the printed circuit board.

4. The toothbrush according to claim 2 further comprising a seal layer between the printed circuit board and the melt matte that seals the front surface of the printed circuit board and the pressure sensitive switch.

5. The toothbrush according to claim 2 wherein the melt matte comprises a protuberance extending from the rear surface of the melt matte, the protuberance actuating the pressure sensitive switch.

6. The toothbrush according to claim 2 wherein the indicator is a light source.

7. The toothbrush according to claim 6 further comprising a light transmissive elastomeric material coupled to the head portion that overlies the light source.

8. The toothbrush according to claim 7 wherein the light transmissive elastomeric material comprises a first portion that overlies the light source and a second portion overlying a neck portion of the handle portion, and wherein light generated by the light source is distributed by the light transmissive elastomeric material form the first portion to the second portion.

9. The toothbrush according to claim 7 wherein the light transmissive elastomeric material further comprises a plurality of protuberances extending from a rear surface of a head of the toothbrush for cleansing soft tissue, the cleaning portions of the plurality of cleaning elements extending from a front surface of the head of the toothbrush.

10. The toothbrush according to claim 7 wherein the light transmissive elastomeric material seals the rear surface of the printed circuit board.

11. The toothbrush according to claim 6 wherein the light source is located within a depression formed in a ledge portion of the head portion, the ledge portion extending into the basin.

12. The oral care implement according to claim 2 further comprising:
   a power source located within a cavity formed in the body, and wherein the printed circuit board is operably coupled to the power source; and
   a motion inducing element for imparting motion to the head portion, the motion inducing element operably coupled to the power source.

13. A toothbrush comprising:
   a body comprising a handle portion and a head portion, a basin formed into a front surface of the head portion;
   a cleaning assembly comprising:
      a head plate;
      a plurality of tooth cleaning elements, each of the plurality of tooth cleaning elements comprising a cleaning portion extending from a front surface of the head plate and a base portion extending from a rear surface of the head plate;
      the base portions of the plurality of tooth cleaning elements melted together to form a melt matte adjacent the rear surface of the head plate;
      the head plate of the cleaning element assembly positioned in the basin and connected to the head portion;
   a pressure sensor adjacent a rear surface of the melt matte such that pressure applied to the cleaning portions of the plurality of tooth cleaning elements is transmitted to the pressure sensor;
   an indicator operably coupled to the pressure sensor for generating a user perceptive signal upon the pressure sensor sensing a pressure that exceeds a predetermined threshold;
   a printed circuit board located within the basin, wherein the pressure sensor comprises a pressure sensitive switch operably coupled to the printed circuit board, wherein the indicator is operably coupled to the printed circuit board, and wherein the indicator is a light source; and a light transmissive elastomeric material coupled to the head portion that overlies the light source;

wherein the basin forms a through hole in the head portion, the light transmissive elastomeric material sealing a rear opening of the through hole, and the head plate enclosing a front opening of the through hole.

14. A method of forming a toothbrush comprising:
a) forming a body comprising a handle portion and a head portion, a basin formed in a front surface of the head portion;
b) operably coupling a light source to a rear surface of a printed circuit board and a pressure sensitive switch to a front surface of the printed circuit board, thereby forming a printed circuit board assembly;
c) positioning the printed circuit board assembly within the basin;
d) connecting a pre-formed cleaning element assembly to the head portion so that the pre-formed cleaning element assembly is non-movable relative to the head portion, the pre-formed cleaning element assembly enclosing a front opening of the basin, the pre-formed cleaning element assembly comprising a plurality of tooth cleaning elements and a melt matte formed of base portions of the plurality of tooth cleaning elements melted together, the melt matte movable within the basin such that pressure applied to the plurality of tooth cleaning elements of the pre-formed cleaning element assembly is transmitted to the pressure sensitive switch to activate the light source.

15. The method according to claim 14 wherein step d) comprises forming the pre-formed cleaning element assembly according to the following steps prior to being connected to the head portion:

inserting the plurality of tooth cleaning elements through holes in a head plate so that each of the plurality of tooth cleaning elements comprises a cleaning portion extending from a front surface of the head plate and the base portion extending from a rear surface of the head plate; and melting the base portions of the plurality of tooth cleaning elements to form the melt matte adjacent the rear surface of the head plate.

* * * * *